United States Patent [19]

Burroughs

[11] Patent Number: 5,026,359

[45] Date of Patent: Jun. 25, 1991

[54] ADAPTER WITH ANTISEPTIC AGENT

[75] Inventor: James E. Burroughs, Mount Prospect, Ill.

[73] Assignee: The Kendall Company, Mansfield, Mass.

[21] Appl. No.: 13,489

[22] Filed: Feb. 11, 1987

Related U.S. Application Data

[63] Continuation of Ser. No. 766,180, Aug. 16, 1985, abandoned, which is a continuation of Ser. No. 496,167, May 19, 1985, abandoned.

[51] Int. Cl.$^5$ .............................................. A61M 1/00
[52] U.S. Cl. ...................................... 604/326; 604/84; 210/501
[58] Field of Search ........................... 604/326, 82-84; 210/501

[56] References Cited

U.S. PATENT DOCUMENTS

| | | | |
|---|---|---|---|
| 1,606,366 | 11/1926 | Hillman | 604/83 |
| 1,654,745 | 1/1928 | Miller | 604/83 |
| 1,678,676 | 7/1928 | Lewis | 210/501 |
| 4,417,892 | 11/1983 | Meisch | 604/326 |
| 4,529,398 | 7/1985 | Nong et al. | 604/327 |
| 4,540,489 | 9/1985 | Barnard | 210/501 |

FOREIGN PATENT DOCUMENTS 2355895 11/1973 Fed. Rep. of Germany ...... 210/501

Primary Examiner—Randy C. Shay
Attorney, Agent, or Firm—Alvin Isaacs

[57] ABSTRACT

An adapter comprising, an outer tube, and an inner tube defining a cavity between the inner and outer tube, with the inner tube having a plurality of openings extending therethrough. The adapter has a solid antiseptic agent in the cavity.

4 Claims, 1 Drawing Sheet

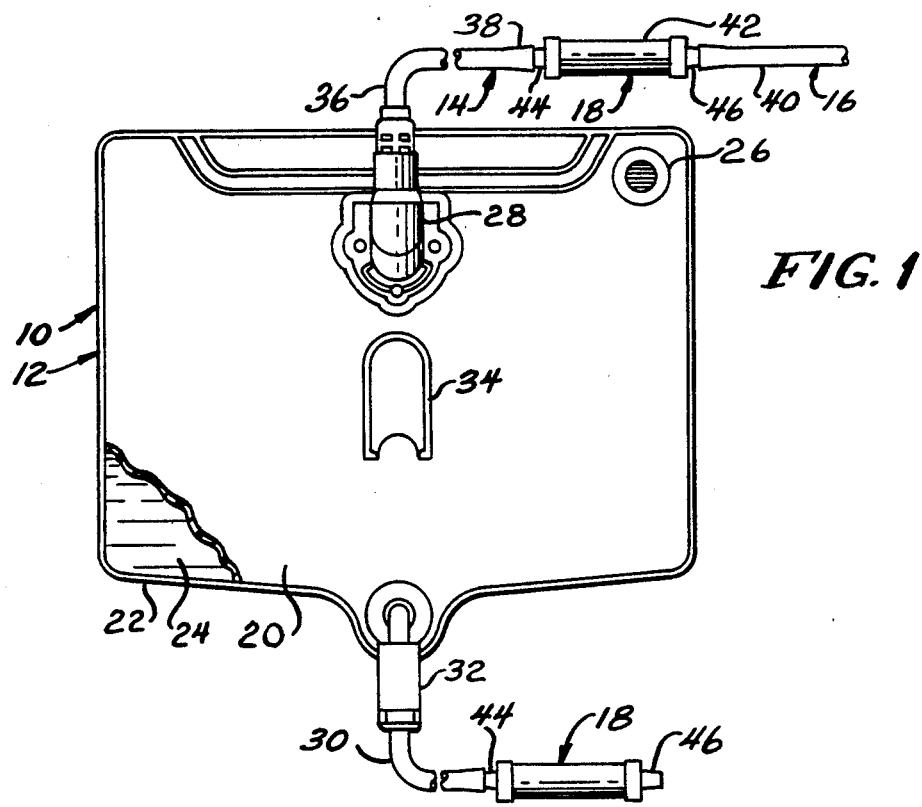

5,026,359

ADAPTER WITH ANTISEPTIC AGENT

This is a continuation of application Ser. No. 766,180, filed Aug. 16, 1985, now abandoned which is a continuation of Ser. No. 496,167, filed May 19, 1983 now abandoned.

BACKGROUND OF THE INVENTION

The present invention relates to adapters, and more particularly to adapters for liquid drainage systems.

Urine drainage systems have been known in the past. Such system normally comprise a receptacle having a chamber, a drainage tube having a downstream end communicating with the chamber, and a catheter having a proximal end connected to an upstream end of the drainage tube. The catheter is passed through the urethra of a patient until a distal end of the catheter is located in the patient's bladder. In use, urine drains the catheter and drainage tube into the receptacle chamber for retention therein.

The receptacles of such systems normally have a tubular section communicating with a lower portion of the chamber. In use, the tubular section is opened in order to periodically that the tubular section is a source of entry of bacteria into the system, since the tubular section is periodically opened to the atmosphere, and is manipulated by the nonsterile hands of hospital personnel. Hence, it is desirable to eliminate this source of bacteria, since the bacteria by retrograde movement may pass into the bladder with possible deleterious results to the patient.

SUMMARY OF THE INVENTION

A principal feature of the present invention is the provision of an adapter for a liquid drainage system.

The adapter of the present invention comprises, an outer tube, and an inner tube defining a cavity between the inner and outer tube, with the inner tube having a plurality of openings extending therethrough.

A feature of the present invention is the provision of a solid or semi-solid antiseptic agent in the cavity. As used herein, the term solid will include semi-solid, such as a gel.

Another feature of the invention is that the antiseptic agent is activated to kill bacteria when urine drains through the inner tube and through the openings onto the antiseptic agent.

Yet another feature of the invention is that the adapter may be connected to a tubular section which communicates with a lower portion of the receptacle.

Still another feature of the invention is that the adapter may be connected to an upstream portion of a drainage tube which communicates with an upper portion of the receptacle.

A further feature of the invention is the provision of other embodiments of the adapter.

Further features will become more fully apparent in the following description of the embodiments of this invention and from the appended claims.

DESCRIPTION OF THE DRAWINGS

In the drawings:

FIG. 1 is a fragmentary elevational view of a liquid drainage system containing an adapter of the present invention; and FIGS. 2-6 are sectional views illustrating various

DESCRIPTION OF THE PREFERRED EMBODIMENTS

Referring now to FIGS. 1 and 2, there is shown a liquid drainage system 10 comprising a receptacle 12, a drainage tube 14, a catheter 16, and an adapter 18. The receptacle 12 has a front wall 20 of flexible plastic material, and a back wall 22 of flexible plastic material, with the front and back walls 20 and 22 being joined at their periphery in order to define a chamber 24 intermediate the front and back walls 20 and 22. The receptacle 12 may have a vent 26 having a bacteria filter of known type in order to filter bacteria from the air passing from the atmosphere through the vent 26 into the chamber 24. The receptacle 12 has a connector 28 attached to the front wall 20, such that the connector 28 communicates with an upper portion of the chamber 24. The receptacle 12 has a tubular section 30 communicating with a lower portion of the chamber 24, and a clamp 32 of known type on the tubular section 30. When it is desired to drain urine from the chamber 24, the clamp 32 is opened in order to permit passage of the urine through the tubular section 30. As shown, the adapter 18 is connected to an outer end of the tubular section 30, and the adapter 18 may be placed in a pocket 34 on the front wall 20 in a storage position of the tubular section 30 and adapter 18 after the clamp 32 has been closed.

The drainage tube 14 has a downstream end 36 connected to the connector 28, such that the drainage tube 14 communicates with the chamber 24 through the connector 28. The drainage tube 14 also has an upstream end 38, and the catheter 16 has a proximal end 40 located outside the patient's body.

The adapter 18 has an outer cylindrical tube 42 having opposed hollow tapered ends 44 and 46. The adapter 18 has an inner cylindrical tube 48 which is spaced from the outer tube 42 in order to define a cavity 50 therebetween, with the inner tube 48 defining a channel 51. As shown, the inner tube 48 has a plurality of openings 52 extending therethrough which communicate between the channel 51 and the cavity 50. The adapter 18 has a solid antiseptic agent 54 received in the cavity 50. A suitable antiseptic agent comprises the following: polyvinylpyrrolidone-iodine, hexachlorophene, chlorhexidine gluconate, paraformaldehyde, hypochlorous acid salts, metal peroxides, p-chlorotaxylenol, or phenylmercuric acetate.

As shown, the adapter 18 may be connected to the outer end of the tubular section 30. Also, the adapter 18 may be connected between the upstream end 38 of the drainage tube 14 and the proximal end 40 of the catheter 16. In both cases, the tapered outer ends 44 and 46 of the adapter 18 are received in the tubes or catheter.

In use, when urine drains through the adapter 18, the urine passes through the openings 52 and onto the antiseptic agent 54 in order to activate the agent 54 and thus kill bacteria in the urine. In this manner, the passage of bacteria through the tubular section 30 and into the chamber 24 is minimized. Also, the adapter 18 minimizes the passage of bacteria into the catheter 16.

Another embodiment of the present invention is illustrated in FIG. 3, in which like reference numerals designate like parts. In this embodiment, the adapter 18 also has an outer tube 42 defining a chamber 56. The adapter 18 has an elongated cylindrical solid antiseptic agent 58 of the type previously discussed, with the agent 58 having a bore 60 extending therethrough. In use, the urine passes through the bore 60 in order to activate the agent 58 and kill bacteria in a manner as previously described.

Another embodiment of the present invention is illustrated in FIG. 4, in which like reference numerals designate like parts. In this embodiment, the adapter 18 also has an outer tube 42 defining a chamber 56. The adapter 18 has a sheet 62, such as paper, wound into a roll and defining a bore 64 extending therethrough. The sheet 62 has a coating of an antiseptic agent as previously discussed on a surface of the sheet 62, such that urine passing through the sheet 62 activates the antiseptic agent on the sheet 62 in order to kill bacteria in a manner as previously discussed.

Another embodiment of the present invention is illustrated in FIG. 5, in which like reference numerals designate like parts. In this embodiment, the adapter 18 has an outer tube 42 defining a chamber 56. The adapter 18 has an elongated generally cylindrical solid antiseptic agent 66 of the type previously discussed received in the chamber 56, with at least a portion of the agent 66 being spaced from the tube 42. In use, urine drains around the agent 66 in order to activate the agent 66 and kill bacteria in the urine in a manner as previously discussed.

Another embodiment of the present invention is illustrated in FIG. 6, in which like reference numerals designate like parts. In this embodiment, the adapter 18 also has an outer tube 42 defining a chamber 56. The adapter 18 has a vial 68 with walls of liquid pervious material, such as cellulose paper. The vial has a cap or stopper 70 received in an open end of the vial 68 in order to close the vial 68. As shown, the vial 68 has a solid antiseptic agent 72, preferably in particulate form, received in the vial 68. In use, urine passes into the chamber 56 and through the walls of the vial 68, and the agent 72 leaches through the vial walls 68 in order to kill bacteria in the urine in a manner as previously discussed. In this embodiment, a suitable antiseptic agent 72 is povidone iodine powder.

The foregoing detailed description is given for clearness of understanding only, and no unnecessary limitations should be understood therefrom, as modifications will be obvious to those skilled in the art.

I claim:

1. An adapter for use with a collection device for urine, comprising:
   a tube defining a chamber;
   a vial received in the chamber and having closed liquid pervious walls constructed from cellulose paper such that the urine passes through the closed walls;
   a closed cap releasably closing the vial; and
   a solid antiseptic agent received in the vial.

2. The adapter of claim 2 wherein said agent is in a particulate form.

3. The adapter of claim 1 including a receptacle having a chamber, and a drainage tube communicating with the chamber, said adapter being connected to an upstream portion of the drainage tube.

4. The adapter of claim 1 including a receptacle having a chamber, and a tubular section communicating with a lower portion of the chamber, said adapter being connected to the tubular section.

* * * * *